(12) United States Patent

Maullu

(10) Patent No.: US 12,672,953 B2

(45) Date of Patent: Jul. 7, 2026

(54) HANDLING DEVICE WITH INCREASED FUNCTIONALITY FOR HAIR TRANSPLANTATION OPERATIONS AND SURGICAL PROCEDURE

(71) Applicants: Giorgio Maullu, Oristano (IT); Silvano Andreani, Borgo Maggiore (SM)

(72) Inventor: Giorgio Maullu, Oristano (IT)

(73) Assignees: Giorgio Maullu, Oristano (IT); Silvano Andreani, Borgo Maggiore (SM)

( * ) Notice: Subject to any disclaimer, the term of this patent is extended or adjusted under 35 U.S.C. 154(b) by 73 days.

(21) Appl. No.: 18/688,425

(22) PCT Filed: Sep. 2, 2021

(86) PCT No.: PCT/IB2021/000566
§ 371 (c)(1),
(2) Date: Mar. 1, 2024

(87) PCT Pub. No.: WO2023/031636
PCT Pub. Date: Mar. 9, 2023

(65) Prior Publication Data
US 2024/0374370 A1 Nov. 14, 2024

(51) Int. Cl.
*A61F 2/10* (2006.01)
*A61B 17/3205* (2006.01)
(Continued)

(52) U.S. Cl.
CPC .......... *A61F 2/10* (2013.01); *A61B 17/32053* (2013.01); *A61B 34/20* (2016.02);
(Continued)

(58) Field of Classification Search
CPC ................ A61B 17/00; A61B 17/3205; A61B 17/32053; A61B 34/20; A61B 2034/2055; A61B 2034/2065
See application file for complete search history.

(56) References Cited

U.S. PATENT DOCUMENTS

2007/0078475 A1\* 4/2007 Bodduluri ........ A61B 17/32053
606/187
2009/0088720 A1\* 4/2009 Oostman, Jr. ............. A61F 2/10
606/130

(Continued)

FOREIGN PATENT DOCUMENTS

CN 203400185 U 1/2014

OTHER PUBLICATIONS

Office Action issued Aug. 1, 2025 in EP Application No. 21793991.7.

(Continued)

*Primary Examiner* — Vi X Nguyen
(74) *Attorney, Agent, or Firm* — Panitch Schwarze Belisario & Nadel LLP

(57) ABSTRACT

A handling device for hair transplantation operations and the surgical procedure with which to operate is provided. The device includes a main body provided with incision elements and with explantation and implantation elements for the transplantation of at least one follicular unit from the scalp of a patient to a tissue to be treated, and an analysis and verification portion associated with the main body proximate to the explantation and implantation elements and adapted to contain the follicular unit. Image acquisition elements are provided for the acquisition of images of the contents of the analysis and verification portion. The image acquisition elements are functionally associated with at least one screen for displaying the images on an enlarged scale showing the contents of the analysis and verification portion so as to examine and verify the properties of the follicular unit directly from the analysis and verification portion before its implantation.

5 Claims, 12 Drawing Sheets

(51) Int. Cl.
    *A61B 34/20*        (2016.01)
    *A61B 17/00*        (2006.01)

(52) U.S. Cl.
    CPC .............. *A61B 2017/00969* (2013.01); *A61B 2034/2055* (2016.02); *A61B 2034/2065* (2016.02)

(56) References Cited

U.S. PATENT DOCUMENTS

| | | | |
|---|---|---|---|
| 2012/0116417 A1* | 5/2012 | Bodduluri | A61B 34/10 |
| | | | 606/187 |
| 2012/0303044 A1 | 11/2012 | Oostman, Jr. | |

OTHER PUBLICATIONS

International Search Report and Written Opinion issued May 16, 2022 in PCT/IB2021/000566.

* cited by examiner

| SCREEN |
| ANALYSIS AND VERIFICATION UNIT |

23, 23a

SCREEN

ANALYSIS AND VERIFICATION UNIT

SCREEN

ANALYSIS AND
VERIFICATION
UNIT

SCREEN

ANALYSIS AND VERIFICATION UNIT

HANDLING DEVICE WITH INCREASED FUNCTIONALITY FOR HAIR TRANSPLANTATION OPERATIONS AND SURGICAL PROCEDURE

CROSS REFERENCE TO RELATED APPLICATIONS

This application is a Section 371 of International Application No PCT/IB2021/000566, filed Sep. 2, 2021, which was published in the English language on Mar. 9, 2023, under International Publication No. WO 2023/031636 A1, the disclosure of which is incorporated herein by reference.

The present invention relates to a handling device with increased functionality for hair transplantation operations and the surgical procedure with which to operate.

In the hair transplantation sector, the use is known of handling devices which are adapted to the removal and subsequent implantation of follicular units from one region where the hair is thicker (for example the nape of the neck) to a region where hair is thinning.

In more detail, the surgical methodology used nowadays entails the explantation of a follicular unit using a suction instrument provided with a punch in its distal portion, the function of which is to perform a form of core sampling of the follicular unit and of part of the surrounding cutaneous tissue; this is then followed by a stage of analysis and verification of the explanted follicular unit using a microscope, which entails the manipulation and positioning of the follicular unit on a suitable laboratory holder, typically a glass slide.

If, following the analysis and verification operations, the follicular unit meets the necessary requirements for implantation, it is implanted in the scalp of the patient.

This operation first of all entails the incision of the scalp in order to define a hole/cut for grafting, and subsequently the surgeon proceeds with the implantation of the follicular unit that was previously explanted.

Typically, there are three surgical instruments, one dedicated to each individual step, i.e.: a first instrument for the explantation of the follicular unit, a second instrument for creating the hole for grafting and a third instrument for the implantation of the follicular unit.

This conventional surgical technique and these conventional instruments are not devoid of drawbacks, which include first and foremost the fact that, in carrying out the manipulation using tweezers and the microscope analysis on special glass slides of each follicular unit, it is not unusual for the unit to be irreparably damaged, which means it is no longer suitable for grafting.

In fact, the hair bulb of each follicular unit is extremely delicate and sensitive to any type of manipulation.

Another drawback of the conventional surgical technique consists in that the shape structure and the peculiarities of the surgical instruments described above are such as to not enable their straightforward sterilization.

This drawback substantially translates into the fact that for each operation, the instruments need to be replaced with new and sterile instruments (obtained, for example, by virtue of a complex sterilization process).

In fact, hair transplants are a form of cosmetic surgery and require the use of sterilized instruments.

In consideration of the cost that substitution of the surgical instruments for each operation can entail, it is easy to imagine that this practice contributes considerably to the overall cost of the operation.

These costs also rise owing to the need to adopt operating methods (and also sterilization methods) that are highly complex, which require the intervention of specialist technicians (a staff of approximately 3 or 4 persons) for extended periods.

The aim of the present invention is to provide a handling device with increased functionality that is capable of overcoming the above mentioned drawbacks.

Within this aim, an object of the present invention is to provide a handling device and a surgical procedure that are capable of safeguarding the integrity of each explanted follicular unit before its implantation.

Another object of the present invention is to provide a handling device the parts of which that are designed to come into contact with the patient can be sterilized both cold (with liquid) and, subsequently, in an autoclave.

A further object of the present invention is to provide a handling device that avails of technologies that are known per se and that therefore is economically competitive.

This aim and these and other objects which will become more apparent hereinafter are achieved by a handling device with increased functionality for hair transplantation operations, which comprises a main body with an elongated shape structure which is ergonomically shaped to be gripped by a hand of an operator; said main body being provided with incision means and with explantation and implantation means for the transplantation of at least one follicular unit from the scalp of a patient to a tissue to be treated; characterized in that it comprises an analysis and verification portion associated with said main body proximately to said explantation and implantation means and adapted to contain said at least one follicular unit; image acquisition means also being comprised which are associated with said analysis and verification portion for the acquisition of images of the contents of said analysis and verification portion; said image acquisition means being functionally associated with at least one screen for displaying said images on an enlarged scale showing the contents of said analysis and verification portion in such a manner as to examine and verify the properties of said at least one follicular unit directly from said analysis and verification portion before its implantation.

This aim and these and other objects which will become more apparent hereinafter are achieved by a surgical procedure for hair transplantation operations, characterized in that it comprises the following steps:

provision of a handling device that has incision means, explantation and implantation means, an analysis and verification portion defined proximately to said explantation and implantation means, image acquisition means associated with said analysis and verification portion and comprising at least one still camera configured in such a manner as to frame the contents of said analysis and verification portion and at least one screen defined by an analysis and verification unit which is functionally associated with said image acquisition means;

use of said handling device;

explantation of at least one follicular unit from the scalp of a patient using said explantation and implantation means and its transfer into said analysis and verification portion;

acquisition of images of said least one follicular unit contained in said analysis and verification portion;

transmission of said acquired images to said analysis and verification unit;

display of said images on an enlarged scale showing said at least one follicular unit on said at least one screen for their viewing by an operator;

examination and verification, by said operator, of the properties of said at least one follicular unit directly from said analysis and verification portion.

Further characteristics and advantages of the invention will become more apparent from the detailed description of a preferred, but not exclusive, embodiment of a handling device with increased functionality for hair transplantation operations, illustrated by way of non-limiting example with the aid of the accompanying drawings wherein.

Figure 1:
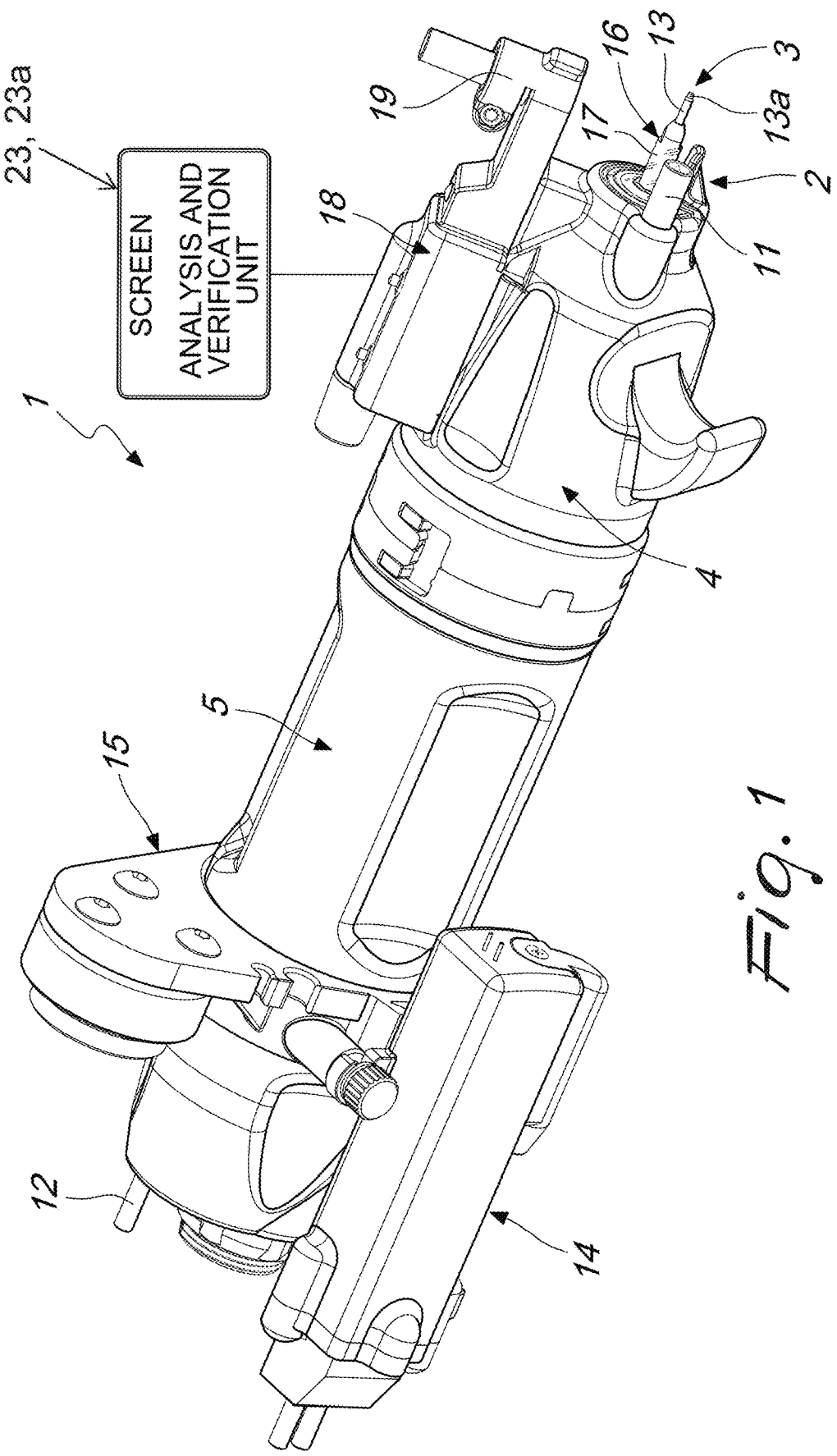
FIG. 1 is a perspective view from the right of a handling device according to the present invention.

With reference to the figures, the handling device with increased functionality for hair transplantation operations, generally designated by the reference numeral 1, comprises a main body with an elongated shape structure which is ergonomically shaped to be gripped by a hand of an operator.

In more detail, such main body is provided with incision means 2 and with explantation and implantation means 3 for the transplantation of at least one follicular unit from the scalp of a patient to a tissue to be treated.

Advantageously, the main body comprises at least one distal section 4 and at least one proximal section 5 which are detachably mutually associated.

Figure 5:
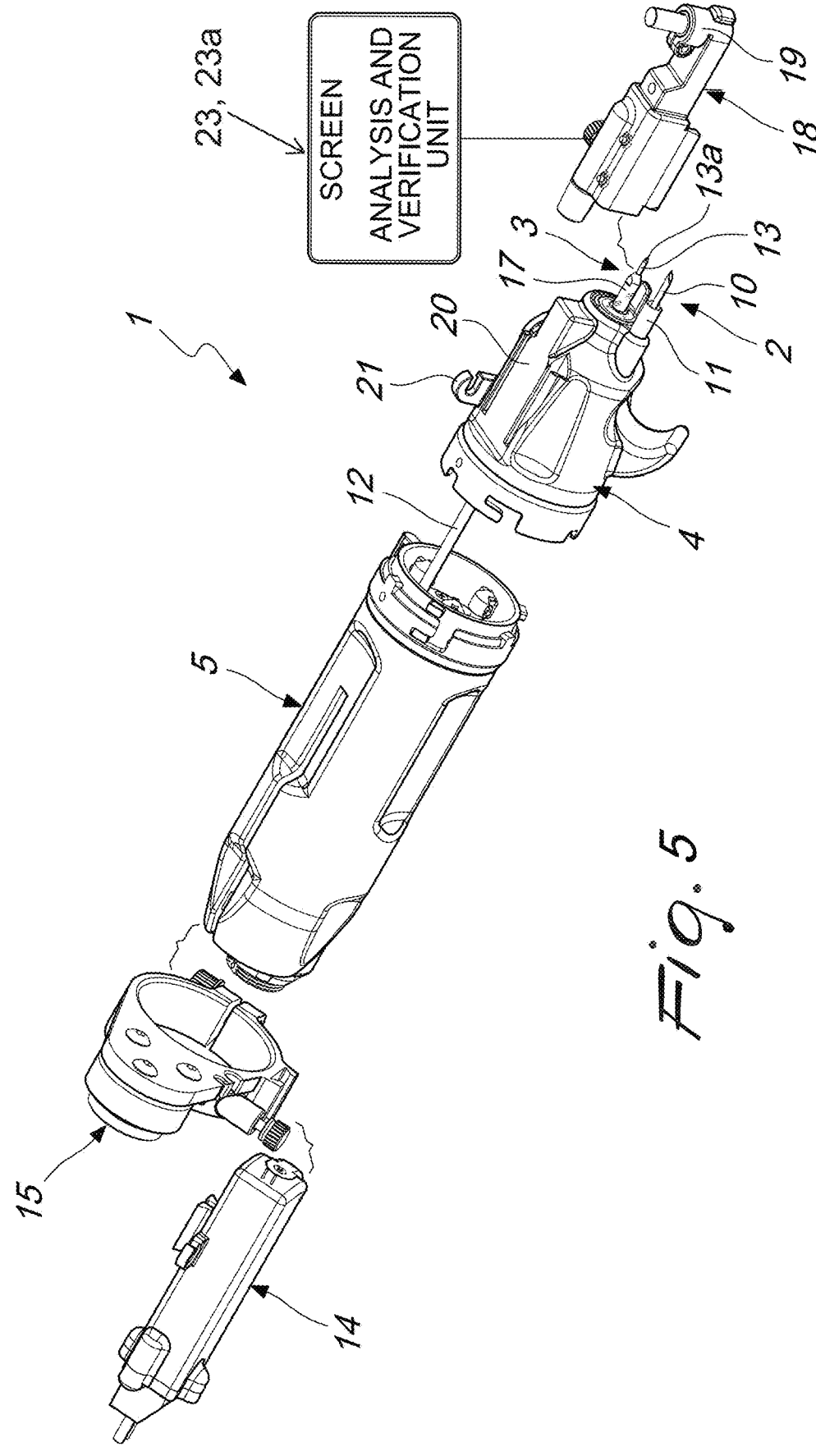
FIG. 5 is a partially exploded perspective view from the right of the handling device shown in the previous figures.
Figure 6:
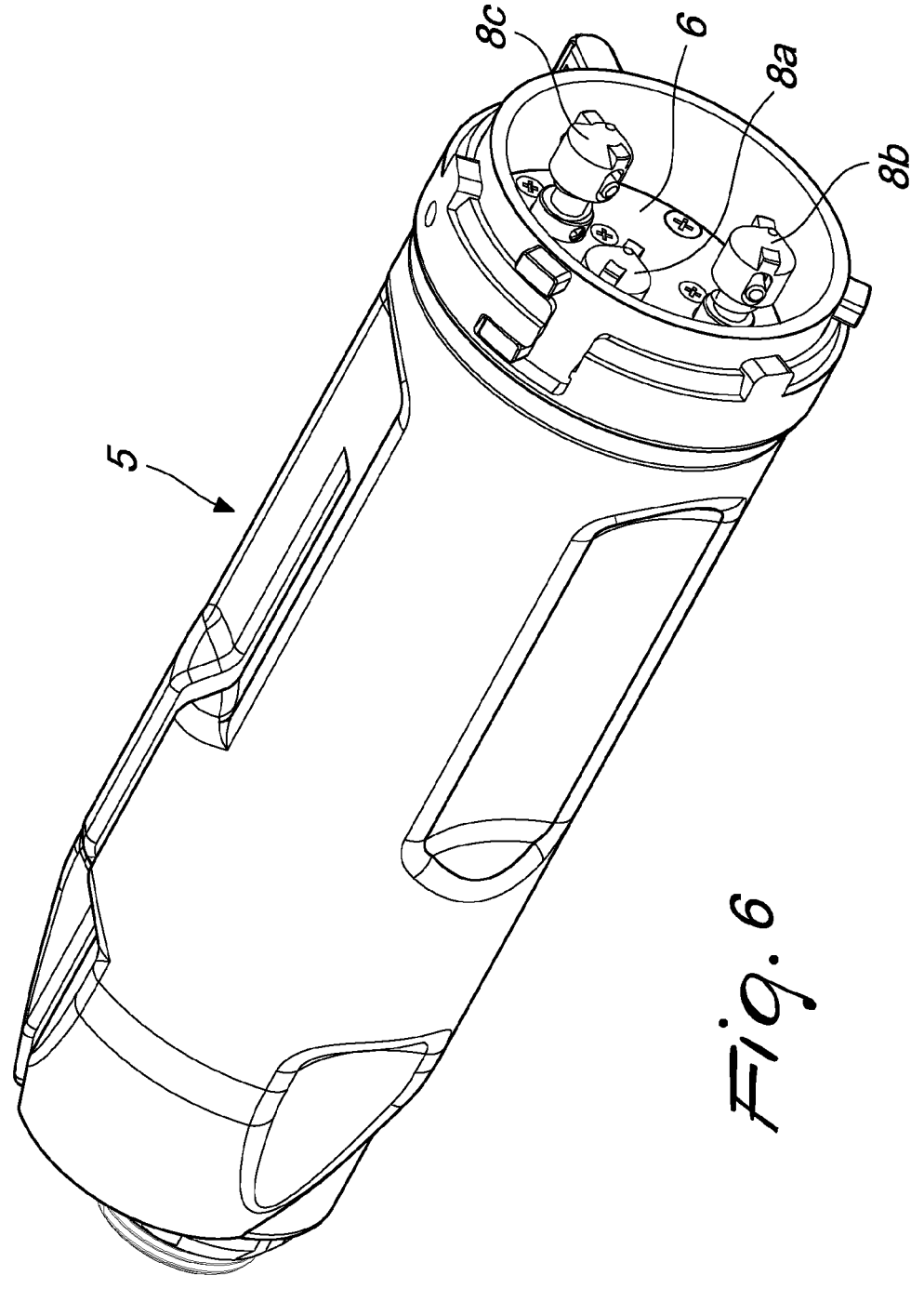
FIG. 6 is a perspective view from the right of the proximal section of the handling device shown in the previous figures.

In the embodiment proposed, this mutual association is achieved with a shape coupling connector of the bayonet type, as shown in FIG. 5.

Conveniently, the proximal section 5 encloses drive means inside it which are not shown for the sake of graphic simplicity and are associated with the incision means 2 and with the explantation and implantation means 3 for their functional movement and these latter means are both associated with the distal section 4 in such a manner as to be separable from the drive means and be subjected to surgical sterilization procedures such as, for example, cold sterilization and subsequent sterilization in an autoclave.

In more detail, the mentioned drive means comprise micro-motors of the brushless type and between the interface surfaces 6 and 7, respectively, of the proximal section 5 and of the distal section 4 there are mechanical interconnection means 8a, 8b, 8c, 9a, 9b and 9c, which are known per se and therefore not described in detail, for the kinematic association of the drive means with the incision means 2 and with the explantation and implantation means 3.

Figure 2:
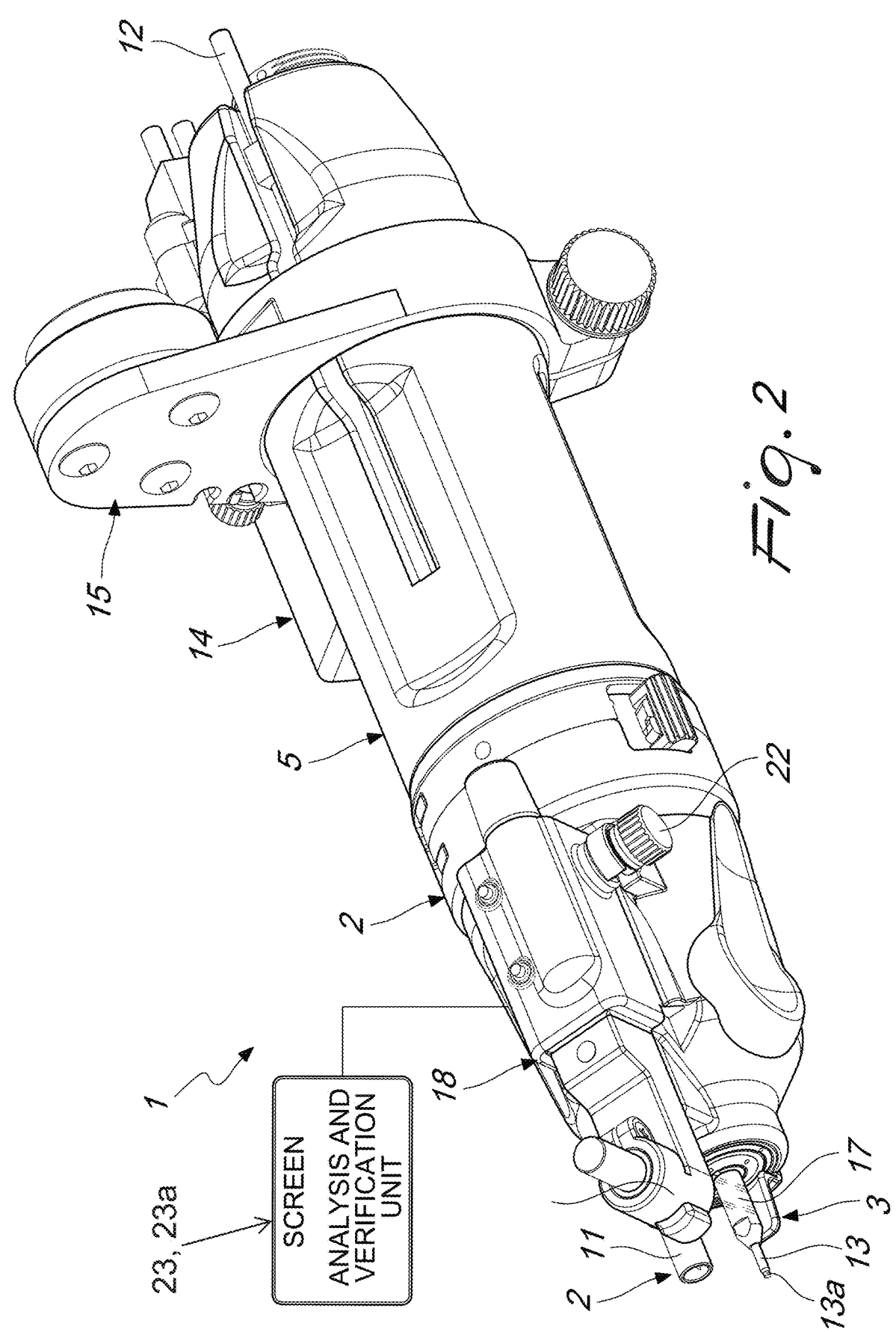
FIG. 2 is a perspective view from the left of the handling device shown in FIG. 1.
Figure 3:
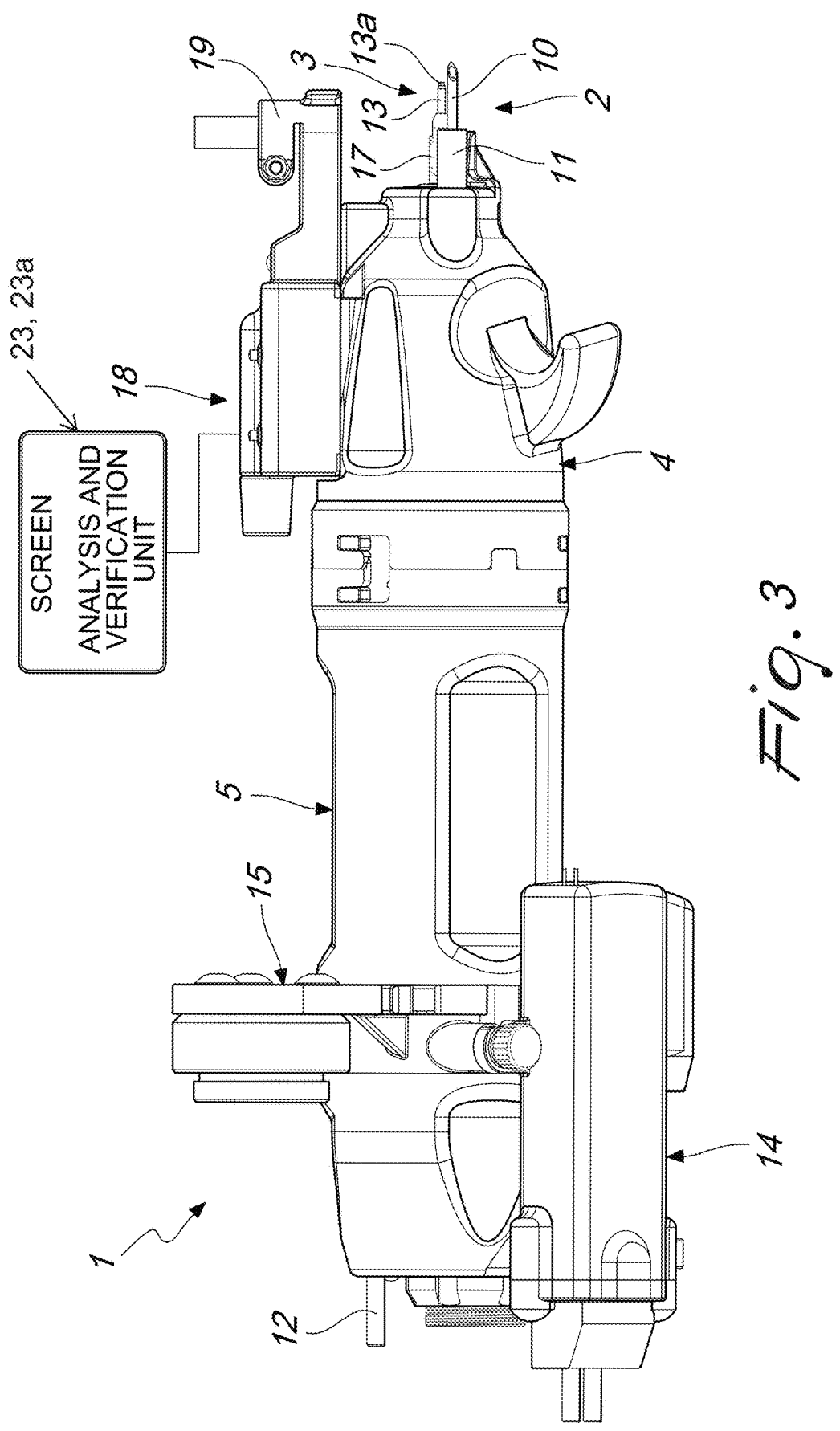
FIG. 3 is a side view from the right of the handling device shown in the previous figures.
Figure 4:
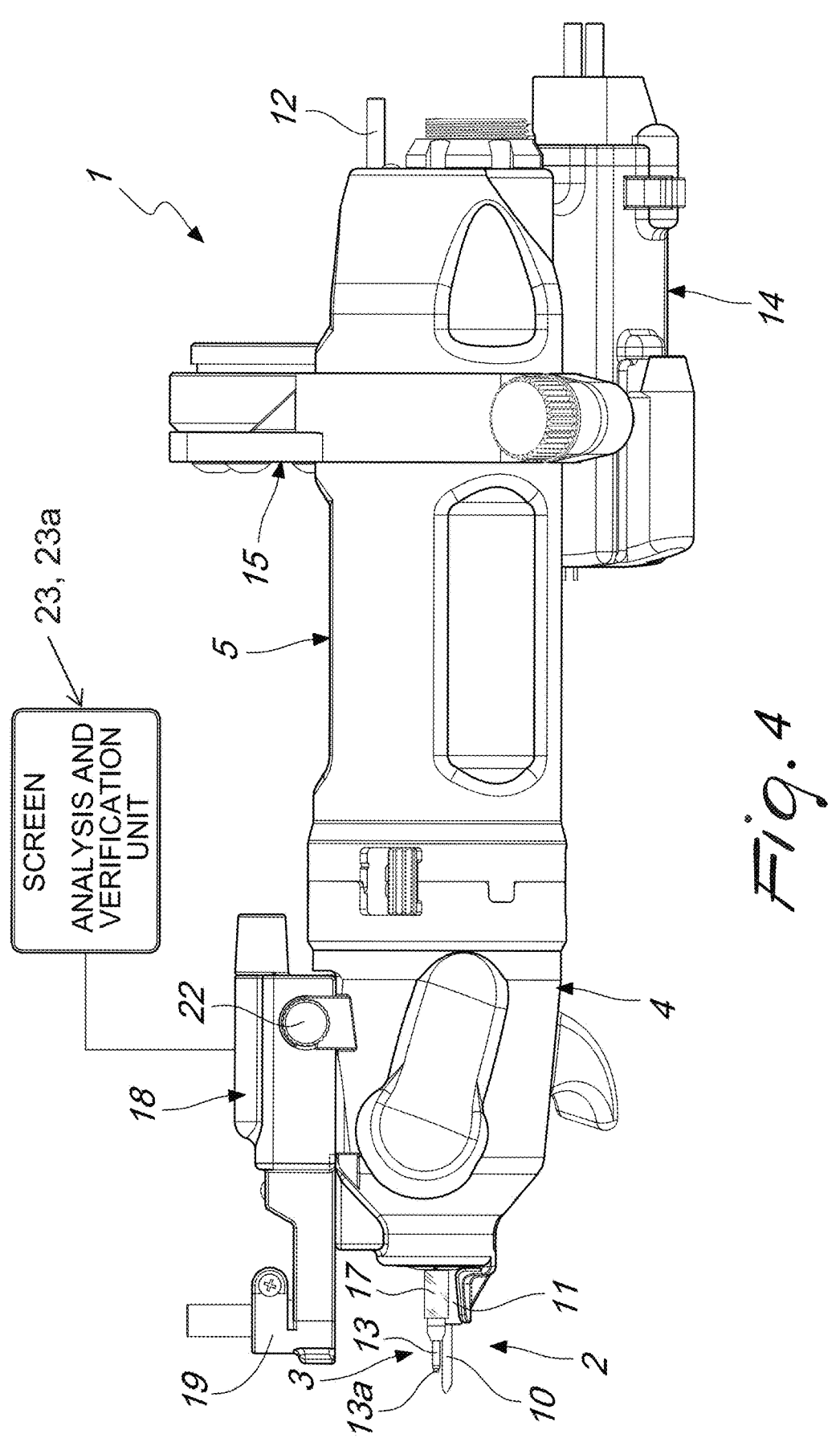
FIG. 4 is a side view from the left of the handling device shown in the previous figures.
Figure 7:
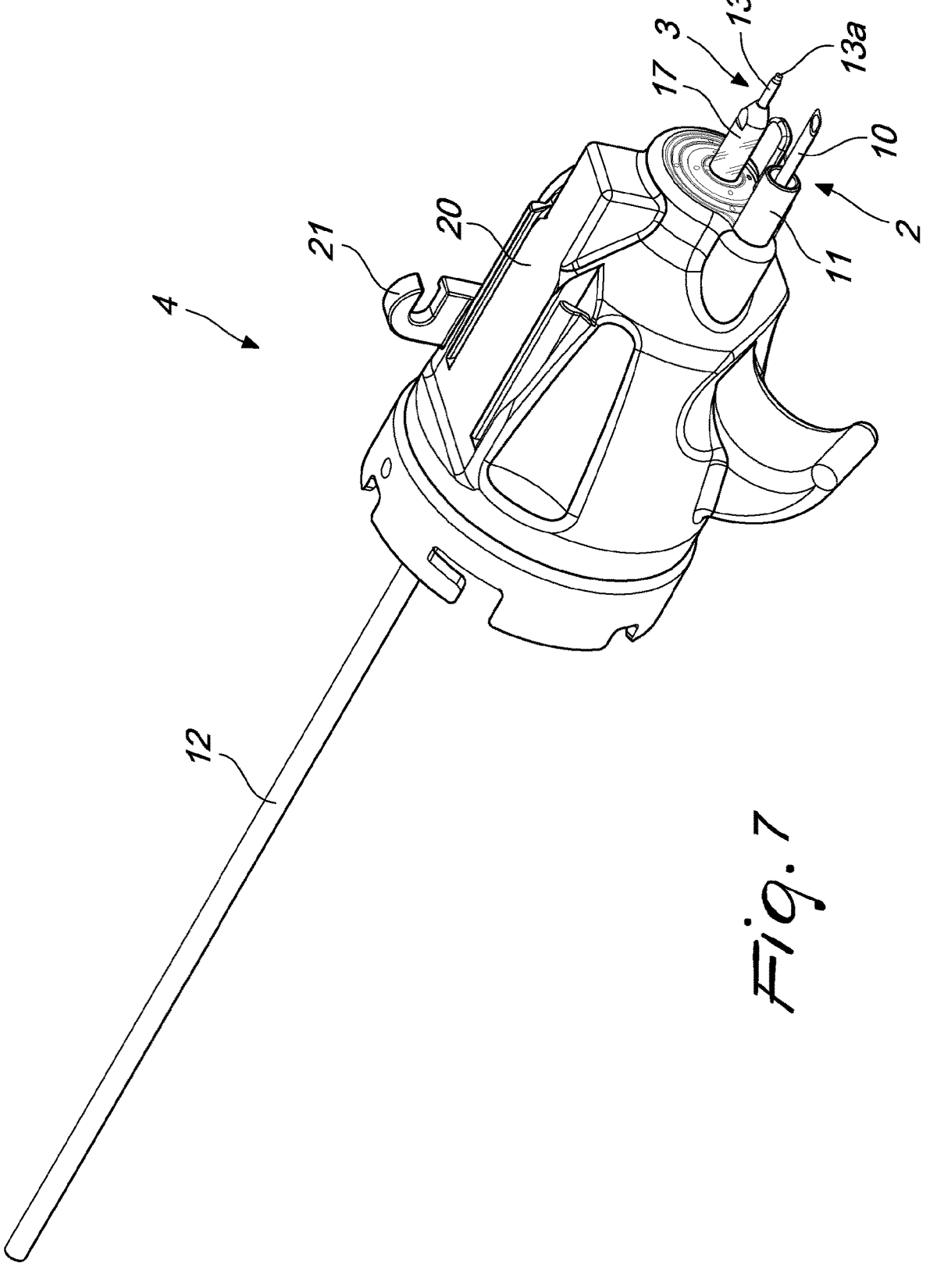
FIG. 7 is a perspective view from the right of the distal section of the handling device shown in the previous figures.
Figure 8:
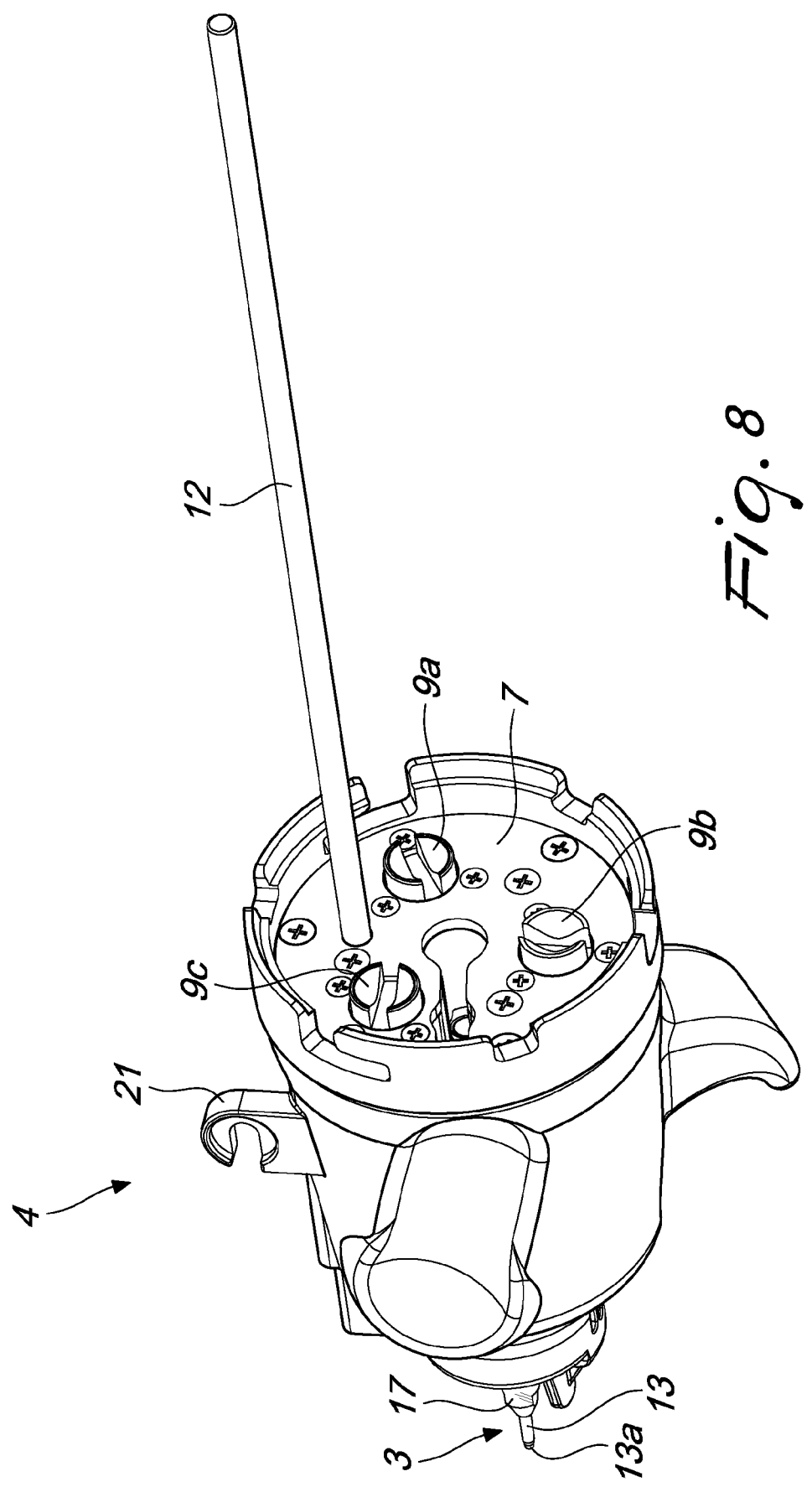
FIG. 8 is a perspective view from the left of the distal section shown in FIG. 7.
Figure 9:
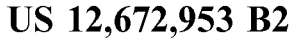
FIGS. 9 to 12 are four perspective views from the left, showing the internal components of the distal section shown in FIGS. 7 and 8.
Figure 10:
Figure 11:
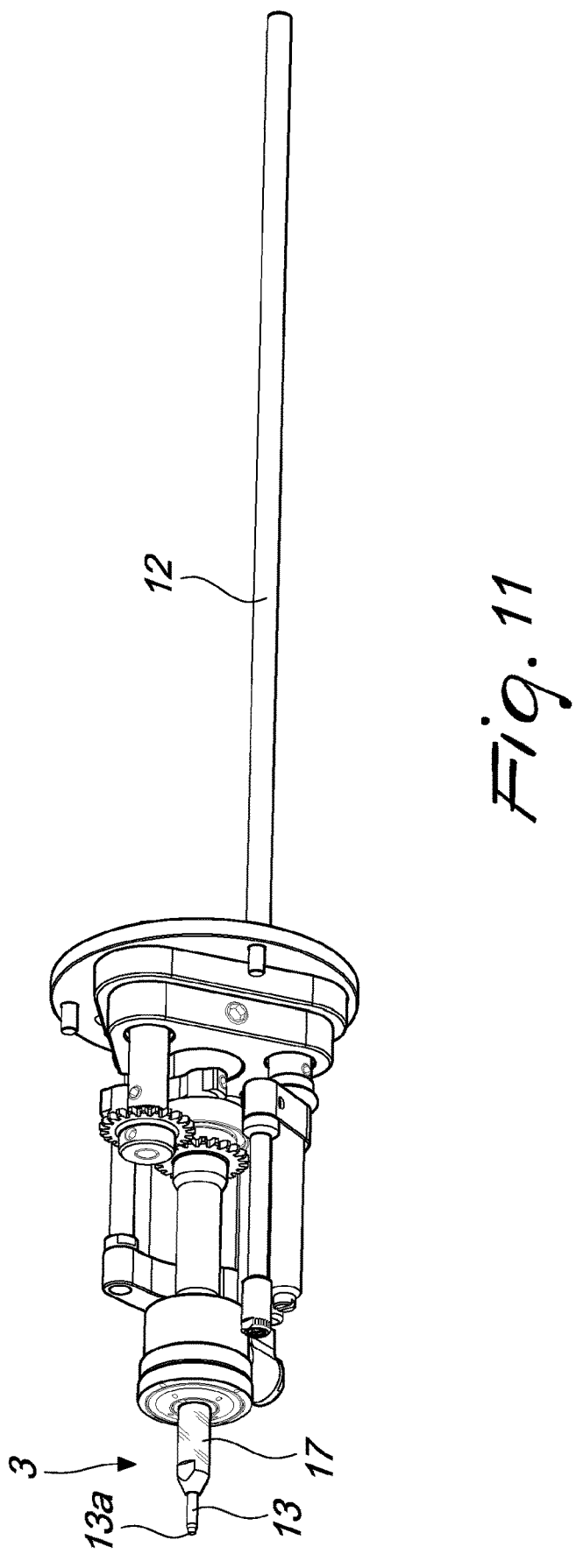
Figure 12:
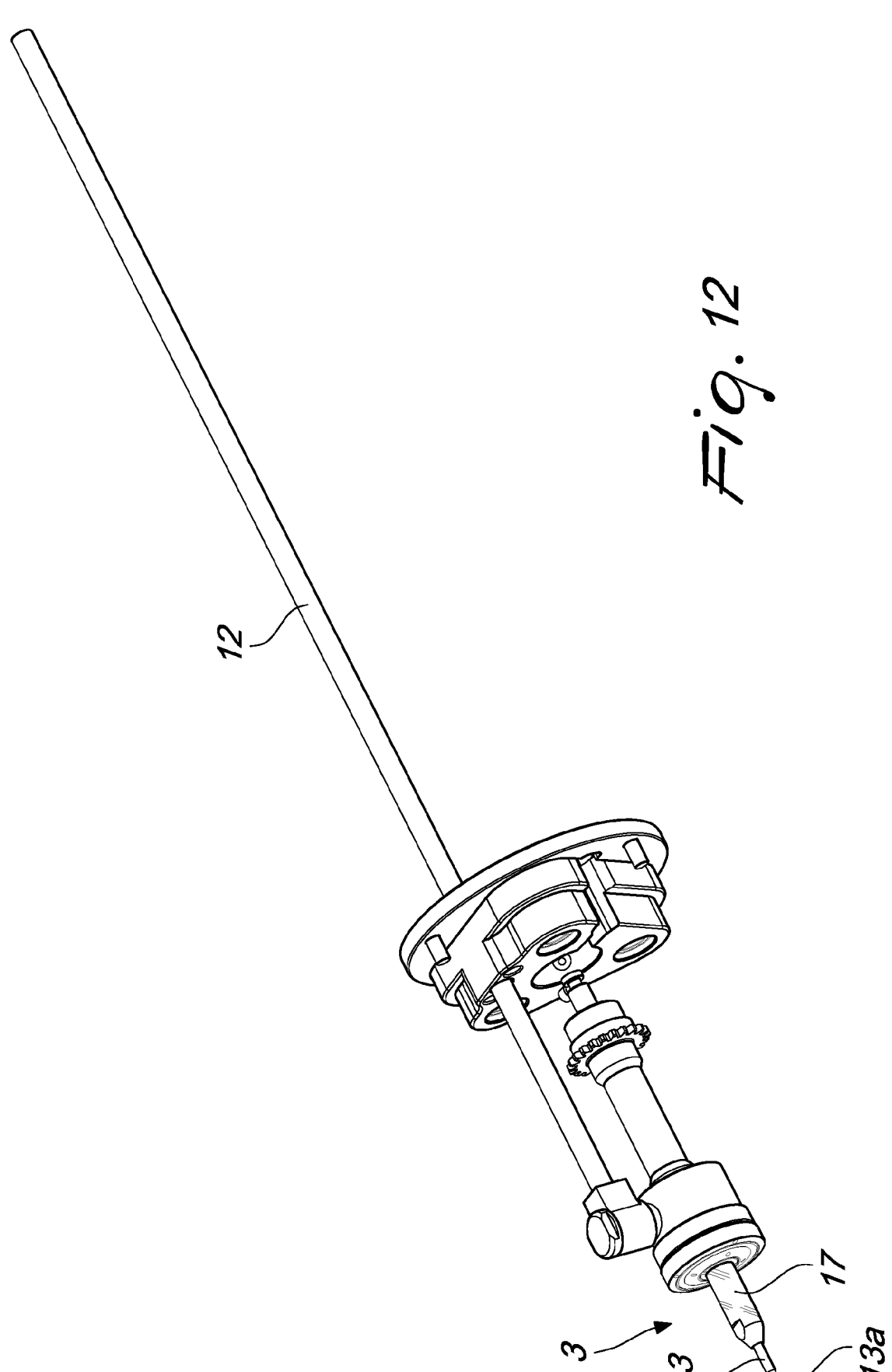

In the embodiment proposed, the incision means 2 comprise a needle 10 (or other instrument provided with a distal cutting edge) of the surgical type that can move via the actuation of the drive means between an inactive position, in which the needle 10 is retracted into the distal section 4, i.e. into a safety cannula 11 as shown in FIGS. 1 to 3, and an incision position, in which the needle 10 is extracted from the distal section 4, as shown in FIGS. 4, 5 and 7.

Advantageously, the needle 10 is of the type that can be disengaged from the distal section 4 for its easy and immediate substitution (it being profitably of the sterilizable and/or single-use type) and is controlled by a first brushless motor the motion of which is transmitted from the proximal section 5 to the distal section 4 via a first pair of mechanical interconnection means 8a and 9a.

Furthermore, the needle 10, controlled by the first brushless motor, can translate in the direction of its longitudinal axis.

In the embodiment proposed, the explantation and implantation means 3 comprise a hollow cannula 12 associated at one end thereof with a punch 13 of the surgical type that can move about its own longitudinal axis via the actuation of the drive means for the core sampling of the follicular unit.

Advantageously, the punch 13 is also of the type that can be disengaged from the distal section 4 for its easy and immediate substitution (the punch 13 can positively also be of the sterilizable and/or single-use type) and is controlled by a respective (second) brushless motor the motion of which is transmitted from the proximal section 5 to the distal section 4 via a respective pair of mechanical interconnection means 8b and 9b.

Conveniently, there are suction means associated with the explantation and implantation means 3 for sucking in the follicular unit during the step of explantation.

A pair of mechanical interconnection means 8c and 9c controls an ejector 13a (understood to be a component adapted to dispense the follicular unit that was previously explanted) which effects the implantation of the follicular unit once the punch 13 has been positioned on the incision that was made previously.

However, the possibility is not ruled out of effecting the re-implantation via a pneumatic actuation (using air flow) that pushes the follicular unit into the incision.

In more detail, such suction means, which are associated with the hollow cannula 12 on the opposite side with respect to the punch 13, comprise a solenoid valve 14 associated with the hollow cannula 12 and associable with an external suction apparatus.

In the embodiment, this solenoid valve 14 is detachably associated with the proximal section 5 via a fixing collar 15.

According to the invention, the handling device 1 comprises an analysis and verification portion 16 which is associated with the main body proximately to the explantation and implantation means 3 and is adapted to contain the follicular unit.

In more detail, the analysis and verification portion 16 comprises at least one suction conduit 17, made of a material transparent to light, such as for example glass, which is directly associated with the explantation and implantation means 3 and adapted to contain the follicular unit.

In the embodiment proposed, the suction conduit 17 is interposed between the hollow cannula 12 and the punch 13. The suction conduit 17 and the punch 13 are generally identified as a single component known as a corer.

Furthermore, there are command and image acquisition means 18 associated with the analysis and verification portion 16 for the acquisition of images of its contents.

The command and image acquisition means 18 comprise control elements for the operator (with which he or she can activate the handpiece 1 in conformance with the current specific operating phase), in addition to specific optical sensors of the type of a micro-camera, a still camera, a photocell and the like.

The command and image acquisition means 18 are functionally associated with at least one screen 23*a* for displaying the images on an enlarged scale showing the contents of the analysis and verification portion 16 in such a manner as to examine and verify the properties of the follicular unit directly from the analysis and verification portion 16 before its implantation, without the necessity of having to manipulate it in any way and without the use of external microscopes.

In the embodiment proposed, such image acquisition means 18 comprise at least one still camera/micro-camera 19 which is configured in such a manner as to frame the contents of the analysis and verification portion 16 and is associated with the distal section 4 via a slider 20 provided with a fastening hook 21 which can engage with a fastening screw 22 associated with the still camera 19 for its locking.

With regard to the screen 23*a*, shown schematically for the sake of graphic simplicity, it is defined by an analysis and verification unit 23 external to the handling device 1 and the image acquisition means 18 are functionally associated therewith for sending the images acquired and displaying them on this screen 23*a*.

According to the invention, the surgical procedure for hair transplantation operations, which can be carried out using a handling device 1 like the one just described, comprises the following steps:

provision of a handling device 1 that has incision means 2, explantation and implantation means 3, an analysis and verification portion 16 defined proximately to the explantation and implantation means 3, image acquisition means 18 associated with the analysis and verification portion 16 and comprising the still camera 19 configured in such a manner as to frame the contents of the analysis and verification portion 16 and at least one screen 23*a* defined by an analysis and verification unit 23 which is functionally associated with the image acquisition means 18;

use of the handling device 1;

explantation of at least one follicular unit from the scalp of a patient using the explantation and implantation means 3, i.e. via the rotation of the punch 13, and its transfer into the analysis and verification portion 16;

acquisition of images of the follicular unit contained in the analysis and verification portion 16;

sending of the acquired images to the analysis and verification unit 23;

display of the images on an enlarged scale showing the follicular unit on the screen 23*a* for viewing by an operator;

examination and verification, by the operator, of the properties of the follicular unit directly from the analysis and verification portion 16.

Conveniently, after the step of examination and verification and if the follicular unit meets the specified requirements for implantation, there is the step of cutting into a tissue to be treated using the incision means 2.

In more detail, the step of incision entails the exit of the needle 10 in such a manner as to cut into (using the handpiece 1 as if it were a scalpel) the tissue to be treated, which can be defined by a region of the scalp of the same patient affected by baldness, and effecting the implantation hole.

At this point comes the step of implantation of the follicular unit in the tissue to be treated using the explantation and implantation means 3.

Alternatively, after the step of examination and verification and if the follicular unit is discarded because it failed to meet the specified requirements, there is the step of expulsion of the follicular unit from the analysis and verification portion 16.

Conveniently, the steps previously described are iterated for the explantation and implantation of a plurality of follicular units.

It should be noted that the step of transferring the explanted follicular unit into the analysis and verification portion 16, i.e. into the suction conduit 17, occurs using suction means associated with the explantation and implantation means 3 in such a manner as to enable the transfer of the explanted follicular unit from the explantation and implantation means 3 into the analysis and verification portion 16 and vice versa without the explanted follicular unit being handled by the operator.

In practice it has been found that the handling device and the surgical procedure, according to the present invention, achieve the set aim and objects in that they make it possible to safeguard the integrity of each explanted follicular unit before its implantation by avoiding the necessity of its having to be handled by the operator.

Another advantage of the device according to the present invention consists in being able to easily separate the sterilizable parts from the non-sterilizable parts in such a manner as to be able to subject the former to sterilization processes and therefore to be able to reuse them.

In particular, in the handling device according to the present invention, all the components subject to sterilization are arranged on the distal section and all the components not subject to sterilization are arranged on the proximal section.

Profitably the handpiece according to the invention can be used even by a single operator (without the need to involve a team of people), also by performing short treatments, for example localized and limited to specific areas of the scalp (thus minimizing the pain after the operation on the patient). The patient can therefore elect, by virtue of the present invention, to undergo many small minimally invasive operations, instead of a single long operation affecting large portions of scalp, as occurs in the known art.

The handling device and the surgical procedure thus conceived are susceptible of numerous modifications and variations, all of which are within the scope of the appended claims.

Moreover, all the details may be substituted by other, technically equivalent elements.

In practice the materials employed, provided they are compatible with the specific use, and the contingent dimensions and shapes, may be any according to requirements.

The invention claimed is:

1. A handling device with increased functionality for hair transplantation operations, which comprises a main body with an elongated shape structure which is ergonomically shaped to be gripped by a hand of an operator; said main body being provided with incision means and with explantation and implantation means for transplantation of at least one follicular unit from the scalp of a patient to a tissue to be treated; further comprising an analysis and verification portion associated with said main body proximate to said explantation and implantation means and configured to contain said at least one follicular unit; image acquisition means also being comprised which are associated with said analysis and verification portion for acquisition of images of contents of said analysis and verification portion; said image acquisition means being functionally associated with at least one screen for displaying said images on an enlarged scale showing the contents of said analysis and verification portion so as to examine and verify properties of said at least one follicular unit directly from said analysis and verification portion before its implantation, wherein said at least one screen is defined by an analysis and verification unit and wherein said image acquisition means are functionally associated with said analysis and verification unit for transmission and display of the images acquired on said at least one screen.

2. The handling device according to claim 1, wherein said analysis and verification portion comprises at least one suction conduit, made of a material transparent to light, which is directly associated with said explantation and implantation means and configured to contain said at least one follicular unit.

3. The handling device according to claim 1, wherein said image acquisition means comprise at least one still camera which is configured to frame the contents of said analysis and verification portion.

4. The handling device according to claim 1, wherein said analysis and verification unit is external with respect to said handling device.

5. A method of analysis and verification of at least one follicular unit using a handling device according to claim 1, further comprising the following steps:

acquiring images of at least one follicular unit contained in said analysis and verification portion;

transmitting said acquired images to said analysis and verification unit;

displaying said acquired images on an enlarged scale on said at least one screen for their viewing by an operator.

\* \* \* \* \*